United States Patent
Bencteux et al.

(10) Patent No.: US 9,192,745 B2
(45) Date of Patent: Nov. 24, 2015

(54) MODULE AND METHOD FOR FLEXIBLE MEDICAL TRAINING BODIES AND EXTENSIONS ROBOTIZED SYSTEM COMBINES

(75) Inventors: Philippe Bencteux, Bois-Guillaume (FR); Sébastien Deboeuf, Herblay (FR); Jacques Marignier, Le Mesnil Esnard (FR)

(73) Assignee: Robocath, Rouen (FR)

( * ) Notice: Subject to any disclaimer, the term of this patent is extended or adjusted under 35 U.S.C. 154(b) by 501 days.

(21) Appl. No.: 13/606,860

(22) Filed: Sep. 7, 2012

(65) Prior Publication Data
US 2013/0172738 A1 Jul. 4, 2013

(30) Foreign Application Priority Data
Sep. 7, 2011 (FR) .................................... 11 57942

(51) Int. Cl.
*A61M 25/01* (2006.01)
*A61B 19/00* (2006.01)
*A61M 5/00* (2006.01)

(52) U.S. Cl.
CPC ........ *A61M 25/0147* (2013.01); *A61B 19/2203* (2013.01); *A61M 5/007* (2013.01); *A61M 25/0113* (2013.01); *A61B 2019/2211* (2013.01)

(58) Field of Classification Search
USPC ....................................................... 600/434
See application file for complete search history.

(56) References Cited

U.S. PATENT DOCUMENTS 5,882,294 A 3/1999 Storz et al.
6,069,420 A * 5/2000 Mizzi et al. ............. 310/40 MM
7,727,185 B2 6/2010 Weitzner et al.
7,927,310 B2 4/2011 Bencteux et al.
2002/0087048 A1* 7/2002 Brock et al. .................. 600/114
2007/0233045 A1 10/2007 Weitzner et al.
2011/0166513 A1 7/2011 Cohen et al.

FOREIGN PATENT DOCUMENTS

| EP | 1442720 | 8/2004 |
| JP | 2009011330 | 1/2009 |
| JP | 2009106431 | 5/2009 |
| WO | WO 0108561 | 2/2001 |
| WO | WO 2007022395 A1 | 2/2007 |
| WO | WO 2009/137410 A1 | 11/2009 |

(Continued)

OTHER PUBLICATIONS

Search Report for European Patent Application No. EP 12 18 3554. Report dated Dec. 10, 2012.

*Primary Examiner* — Tse Chen
*Assistant Examiner* — Joel F Brutus
(74) *Attorney, Agent, or Firm* — Miller, Matthias & Hull LLP

(57) ABSTRACT

Module for driving an elongated flexible medical device in a first direction, comprising:
  a channel,
  on each side of the channel:
    a first and a second pulley comprising a drive surface,
    an elongated strip comprising a first face and an opposite second face, the first face cooperating with the drive surface of the pulleys, the second face cooperating with the flexible medical device, the strip being stretched by the pulleys with an elongated portion extending into the channel along the first direction,
  at least one of the pulleys being motorized.

15 Claims, 10 Drawing Sheets

(56) References Cited

FOREIGN PATENT DOCUMENTS

| WO | WO 2009120992 | A2 | 2/2010 |
|---|---|---|---|
| WO | WO 2010078344 | A1 | 7/2010 |
| WO | WO 2010081050 | A1 | 7/2010 |
| WO | WO 2011008922 | A2 | 6/2011 |

* cited by examiner

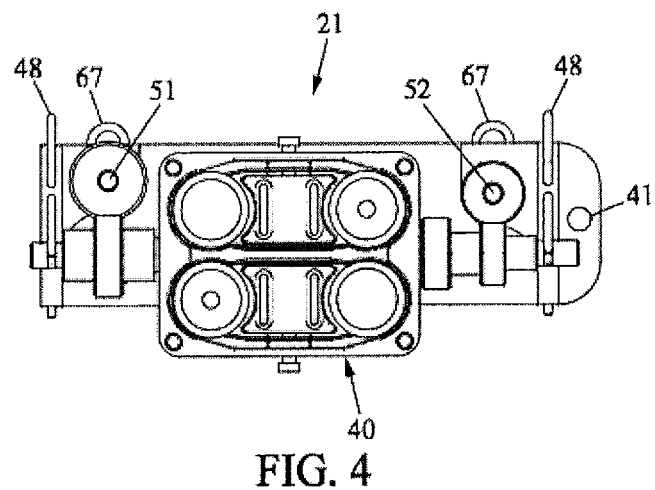
FIG. 4
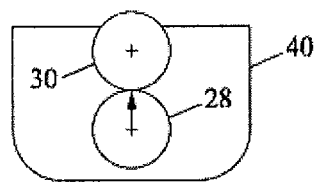
FIG. 11a
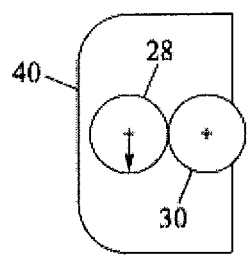 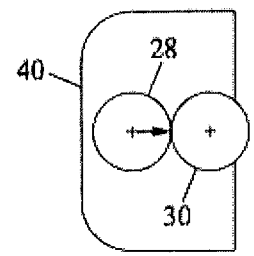
FIG. 11b          FIG. 11c

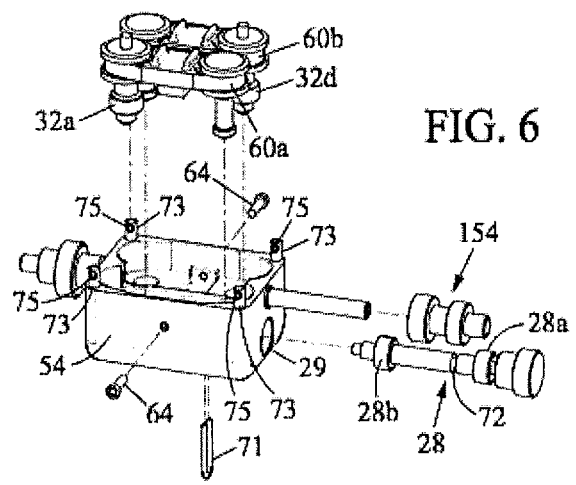
FIG. 6
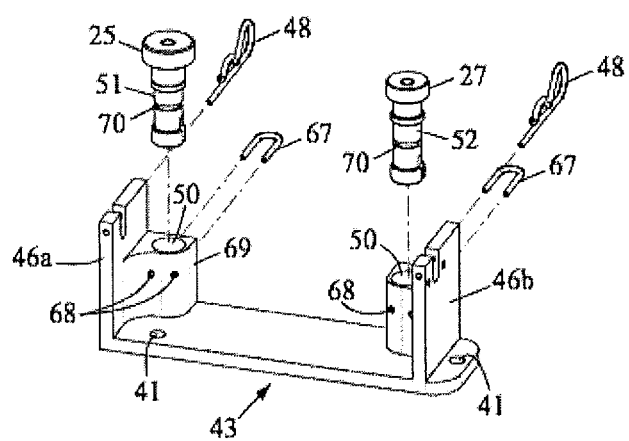

MODULE AND METHOD FOR FLEXIBLE MEDICAL TRAINING BODIES AND EXTENSIONS ROBOTIZED SYSTEM COMBINES

FIELD OF THE INVENTION

The present invention relates to drive modules and methods for elongated flexible medical devices and associated robotic systems.

TECHNOLOGICAL BACKGROUND

More particularly, the invention relates to a module for driving an elongated flexible medical device in a first direction, comprising a base and a movable assembly mounted to rotate on said base about the first direction, with the movable assembly comprising a support.

One typical example of an elongated flexible medical device is, for example, a catheter. Such a catheter must be introduced into an anatomical passageway of a patient, and therefore must be relatively flexible. The end of the catheter must also reach an internal organ of the patient, therefore it must be relatively elongated. Other examples of elongated flexible medical devices are, for example, a guide, which is smaller in diameter and generally arranged inside the catheter and on which the latter slides, or an interventional catheter, also arranged inside the catheter and whose end fulfills a certain medical function, such as a medical tool (clamp, balloon, etc.).

Insertion of such catheters is typically x-ray monitored. This results in exposing the physician who repeatedly performs such insertions to some degree of radiation.

Efforts have been made to robotize such insertion. Here, catheter manipulation is performed by the robot, still using x-ray guidance, the robot being remote-illustrative of such efforts. However, these very complex systems are not well suited for implementation in a hospital setting by staff who are not technically qualified. In addition, the dissociation of translational driving and rotational driving of the catheter makes the implementation of such a system hazardous.

Document U.S. Pat. No. 7,927,310 describes an example of a system according to the preamble of Claim 1.

This system has the great advantage of being well-suited to the sterile nature of catheters or other devices inserted into the patient which are immersed in a preservative fluid such as normal saline. However, in this document, the drive module applies movement to the catheter by 2 wheels arranged on the same side, a third non-driven wheel, arranged on the other side of the catheter, serving to maintain the pressure.

In practice, catheter drive problems have been found with such a mechanism. These problems are particularly due to the flexibility of the catheter and to its preservation in a fluid medium.

The object of this invention is to overcome these drawbacks.

SUMMARY OF THE INVENTION

To that end, according to the invention, a drive module of the type in question comprises:
a channel formed in the support, extending in the first direction,
on each side of the channel:
at least a first pulley and a second pulley, having a drive surface and borne by the support,
an elongated strip comprising a first face and an opposite second face, the first face cooperating with the drive surface of the pulleys, the second face adapted to cooperate with the flexible medical device, the strip being stretched by the pulleys with an elongated portion extending into the channel in the first direction,
at least one of the pulleys being motorized.

With these arrangements, the catheter's linearity is optimized at the drive module, which improves its applied movement.

In preferred embodiments of the invention, it is optionally possible to also use one or more of the following arrangements:
the module further comprises an adjustment device placed between the first and the second pulley, a tensioning surface cooperating with the first face of the strip and movable relative to the channel along an adjustment direction transverse to the first direction;
the first face of the strip has sprockets and the drive surface of the motorized pulley has teeth that mate with said sprockets;
the module comprises a set of driving parts cooperating with each other to transmit a movement from a motor to the motorized pulley;
the movable assembly is mounted to rotate on the base about a first axis, and the channel comprises a portion formed in the support along a second axis, parallel to the first axis and offset relative to it;
the module comprises a lateral adjustment device adapted to adjust an offset between the first and second axis;
the lateral adjustment device comprises a control adapted to cause a clamping of the medical device during a first part of the drive stroke, and to adjust said offset between the first and second axis during a second part of the drive stroke after the first part;
the module is composed of said strips, of sterilizable parts, and of elastically deformable removable assembly parts suitable to hold the sterilizable parts together with freedom of movement relative to each other.

According to another aspect, the invention relates to a robotic system that includes:
such a drive module,
a container suitable to contain an elongated flexible medical device in a sterile aqueous condition, and in communication with said channel,
a motor cooperating with the motorized pulley.

According to one embodiment, the system further comprises a sterile barrier, the motor cooperating with the motorized pulley through the sterile barrier.

According to another aspect, the invention relates to a method of driving an elongated flexible medical device in a first direction, comprising:
a drive module is supplied comprising:
a channel extending in the first direction,
on each side of the channel:
at least a first pulley and a second pulley comprising a drive surface,
an elongated strip comprising a first face and an opposite second face, the first face cooperating with the drive surface of the pulleys, the second face adapted to cooperate with the flexible medical device, the strip being stretched by the pulleys with an elongated portion extending into the channel in the first direction, an elongated flexible medical device is placed in the first direction, partially in said channel, at least one of the pulleys is motorized.

According to another aspect, the invention relates to a robotic arteriography system comprising:

a base equipped with a first transmission device, a module for driving an elongated flexible medical device in a direction of extension, comprising:

a second transmission device suitable for cooperating with the first transmission device, at least one drive device connected to the second transmission device, and suitable for cooperating with an elongated flexible medical device in order to alternately maintain said medical device stationary relative to the base or move said medical device in the direction of extension, a sterility barrier covering the base, the first and second transmission devices cooperating through the sterility barrier, wherein the drive module is composed of a set of disposable parts, a set of sterilizable parts, and a set of elastically deformable assembly parts, said sterilizable parts being held together with freedom of movement by said assembly parts.

According to another aspect, the invention relates to a robotic catheterization system comprising:

a central processing unit, at least a first, second, and third control line respectively suitable for sending a command to a first, second, and third drive motor for the same catheter, wherein the first and second control lines are controlled according to a first predetermined ratio in order to command a pure translation movement of the catheter along its axis, and wherein the first and third control lines are controlled according to a second predetermined ratio in order to command a pure rotation movement of the catheter along its axis.

According to another aspect, an invention relates to a drive module comprising a base and a movable assembly mounted to rotate on said base about the first direction, wherein the movable assembly comprises:

a bottom part comprising at least one drive shaft, and a disposable part in which said channel is formed, the disposable part comprising at least said pulleys, the disposable part being assemblable on the bottom part, the motorized pulley cooperating with said drive shaft.

The disposable part will be discarded after use and replaced by an identical part for future use.

According to another aspect, an invention relates to a module for driving an elongated flexible medical device in a first direction, comprising a base and a movable assembly mounted to rotate on said base about the first direction, the movable assembly comprising a support, wherein the module comprises:

a channel formed in the support and extending in the first direction, on each side of the channel:

at least a first and a second drive device borne by the support, each having a face suitable for cooperating with the flexible medical device, wherein said channel comprises a portion along a second axis, parallel to the first axis and offset relative to it.

In particular, the amplitude of the axial offset may be variable.

Other features and advantages of this invention will become apparent from the following description of several embodiments, given as a non-limiting example and referring to the attached drawings.

BRIEF DESCRIPTION OF THE DRAWINGS

In the drawings:

FIG. 4 is a top view of the module from FIG. 3 after opening the lid, FIG. 6 is an exploded perspective view of the module from FIG. 3, and FIGS. 7a and 7b are top views of the robot in two different positions, FIGS. 11a, 11b, and 11c illustrate various states depending on the command given to the different motors.

In the various figures, the same references designate identical or similar elements.

DETAILED DESCRIPTION

Figure 1:
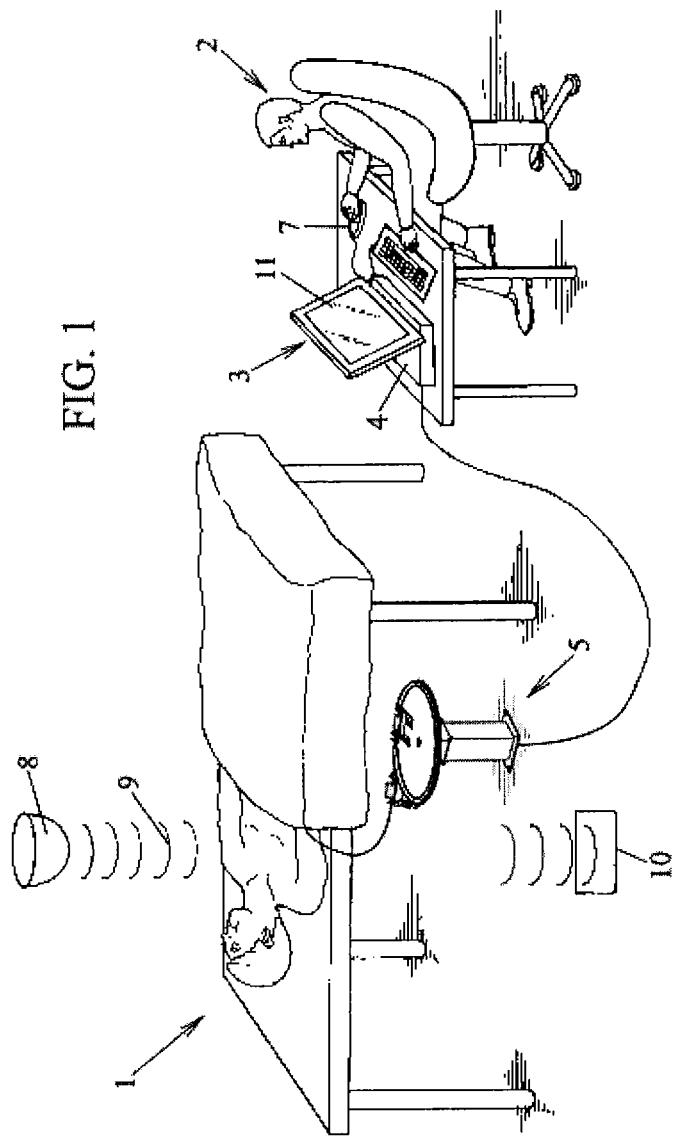
FIG. 1 is a schematic view of a robotized arteriography system according to the invention

In FIG. 1, a patient 1 is undergoing arteriography. This arteriography is performed by personnel 2, such as a surgeon or qualified medical personnel for example, using an automated arteriography system 3 which comprises for example a programmable machine 4 remotely controlling a catheter winder/unwinder 5 arranged in proximity to the patient 1. The winder/unwinder 5 is robotic and is sometimes called the "robot."

The travel of a catheter 6 inside the body of the patient 1 is remotely controlled by the qualified personnel 2 using a control means 7, such as a mouse or a joystick for example, connected to the programmable machine 4.

The installation further comprises an x-ray source 8 emitting x-rays 9 to the patient 1, and an x-ray detector 10 capable of detecting the radiation passing through the patient 1. The detector 10 can be connected to the computer 4 in order to display a detected image on its screen 11.

Figure 2:
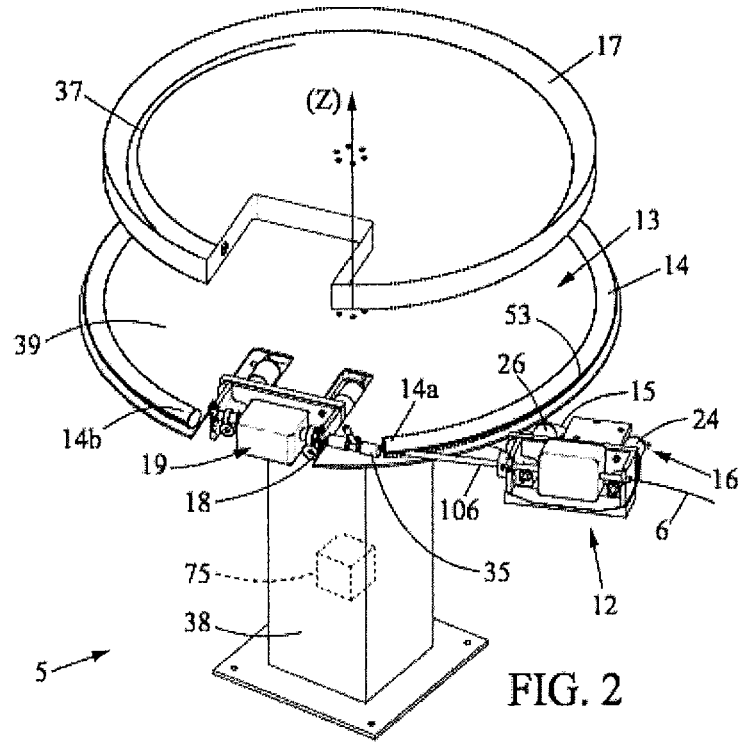
FIG. 2 is a partial exploded perspective view of a catheterization robot.
Figure 3:
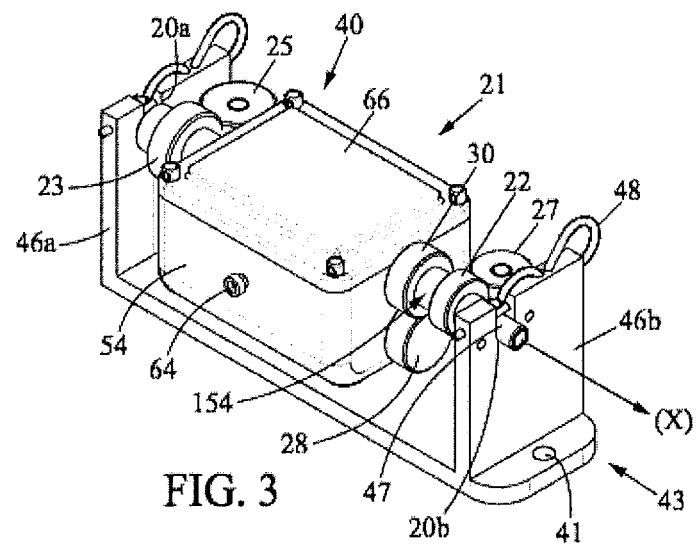
FIG. 3 is a perspective view of a drive module for the robot from FIG. 2.

As shown in FIG. 2, the robot 5 comprises a vertical foot 38, a horizontal tray 39 supported on said foot, and at least a concentric first system 12 and second system 13 arranged around an axis that is, for example, vertically oriented in the direction Z.

The first system 12 comprises a first container 14 in the form of a flexible tube borne by the tray at its periphery, for example that can be snapped into hooks borne by the tray. The flexible tube extends from a first end 14a to a second end 14b, making less than one turn around the tray. The tube 14 receives a tubular catheter 6 intended to be inserted into an artery of the patient 1. The flexible tube 14 comprises a longitudinal slit 53 through which the catheter 6 can enter or exit the tube 14. The flexible tube 14 could be replaced by a rigid tube equipped with a lip allowing the entry/exit of the catheter. A rigid guide tube 106 extends between the longitudinal slit 53 and the drive mechanism 16. It accepts the catheter 6 inside of it. The length of the tube 14 is greater than the conventional length of a catheter. The catheter extends from a first end to a second end in a catheter elongation direction. The tube 14 is also filled with a preservation fluid in which the catheter is immersed. The first system 12 also comprises a drive mechanism 16, or "module," which will be described in more detail below with reference to FIGS. 3 to 6. This drive mechanism is supported by an arm 15 fixedly connected to the foot, and is intended to be placed in immediate proximity to orifice of the patient to be catheterized. The position of the arm 15, particularly its height relative to the ground, can optionally be adjusted to the needs of the operation. The drive mechanism is controlled by the surgeon 2 by using the computer 4.

The second system 13 comprises a second container 17, intended to be fastened to the tray 39. The second system also comprises an exit 18 through which a guide 37 contained in the second container can access the exterior of the second container, and in particular the interior of the first container 14. In particular, it accesses the interior of the catheter contained in the first container.

The second container receives a tubular guide 37 extending between a first and a second end in a guide elongation direction, and is immersed in a fluid suitable for its preservation. Furthermore, the second container also comprises a drive mechanism 19, similar to the first drive mechanism 16 of the first system 12, which will be described below in more detail with reference to FIGS. 3 to 6.

FIGS. 3 to 8 show the first drive mechanism 16 according to an illustrative embodiment. The second drive mechanism 19 may be similarly made. The first drive mechanism 16 comprises a base 43 fastened to the arm 15. As an example, the arm 15 is equipped with a mounting bracket plate 42 drilled with two mounting holes and two motorization holes, and the base 43 has a plate drilled with corresponding holes: mounting holes 41 and motorization holes 50 placed opposite the holes in the plate 42. A sterility barrier 44 extends between the plate 42 associated with the arm 15 and the base 43, being pierced only to allow said mounting devices 45 associated with the mounting holes and the drive shafts associated with the motorization holes 50 to pass through these openings. Thus, the sterility barrier 44 will cover the arm 15, and particularly the motors 24 and 26, with the exception of the base 43 and what it supports. The base 43 supports a movable assembly 40 mounted to rotate relative to the base 43, about an axis of rotation that is the same as the axis X of elongation of the catheter 6, in two bearings 20a, 20b of the base. The base 43 has a U-shaped profile, where the two parallel arms of the U 46a, 46b are used to define the bearings. In particular, the arm 46b comprises a slot 47 open at the top, forming a portion of the bearing, which can be closed with a removable device 48 such as a pin to complete the bearing. A portion of the pin and of the slot together form the bearing. A similar embodiment is provided on the other arm. In the example shown, the movable assembly has a shell 21, which will be described in more detail below, supporting the catheter, a cylindrical rotational gear ring 23 mounted on an upstream cylindrical shaft 49, extending along the axis X, and a translational gear ring mounted on a downstream cylindrical shaft 149, extending along the axis X, with the catheter 6 passing through them both. The aligned upstream 49 and downstream 149 shafts form the translational and rotational drive axis of the catheter.

The first drive mechanism 16 comprises a rotational electric motor 24 (FIG. 2) intended for rotating the catheter around the axis X. Upon command from the computer 4, if electrical current flows, the motor 24 causes rotation of a rotational shaft 51 equipped with a rotational gear 25 that cooperates with the rotational gear ring 23 of the movable assembly. It should be noted that the gears 25 and 23 comprise angled teeth so that the rotation of the gear 25 around an axis transverse to the axis X can generate the rotation of the gear 23 around the axis X.

The drive mechanism 16 also comprises a translational electric motor 26 (FIG. 2) intended for driving the translational movement of the catheter along the axis X. Upon control from the computer 4 if electrical current flows, the motor 26 causes rotation of a translational shaft 52 equipped with a translational gear 27. The translational and rotational shafts 51 and 52 are parallel. A transfer sleeve 154 extends along the X-axis and supports, with an offset along said axis, a translational gear 22 and an intermediate gear 30. The gears 27 and 22 have angled teeth so that the rotation of the gear 27 around an axis transverse to the axis X can generate the rotation of the gear 22 around the axis X.

These motors are, for example, stepper or brushless motors.

The translation gear ring 22 rotationally drives a shaft 28, rotatably mounted in two bearings 29 inside the shell 21, through an intermediate gear 30. The shaft 28 supports a first and a second toothed bearing span 28a, 28b. The shaft 28 may optionally be replaced by a worm gear.

Figure 5:
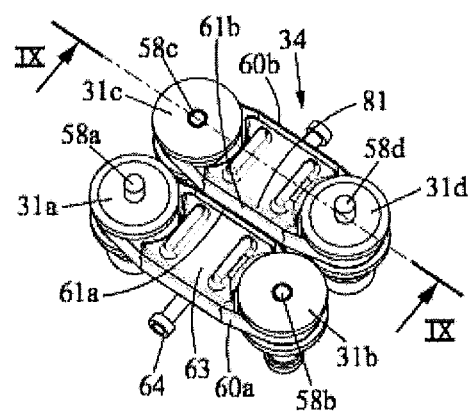
FIG. 5 is an exploded perspective view of the movable assembly of the module from FIGS. 3 and 4.
Figure 5:
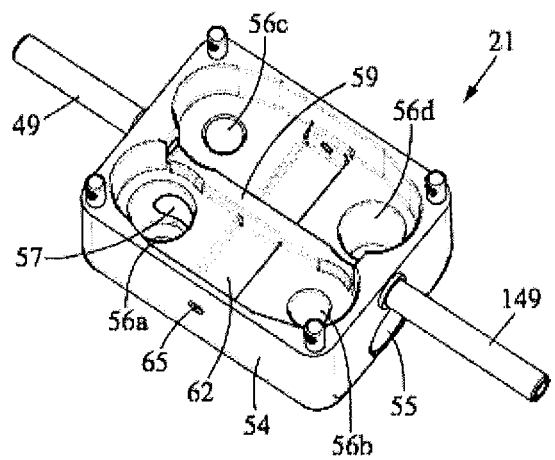

As can be seen in FIG. 5, the shell 21 comprises a bottom part 54 suitable for receiving various elements. A cylindrical hole 55 is visible, extending parallel to the axis X, and forms the two bearings 29 for receiving the shaft 28.

In the shell, there are four cylindrical holes 56a-56d extending parallel to each other in a direction transverse to the direction X and arranged on either side of the axis X. Note that the diagonally opposing cylindrical holes 56a and 56d open into the cylindrical hole 55 through a respective opening 57.

Each of the holes 56a-56d receives a corresponding shaft 58a-58d. The shafts 58a and 58d are identical to one another and comprise, at the opening 57, a sprocket suitable for cooperating with the corresponding toothed bearing span of the shaft 28 such that rotation of the shaft 28 around its axis drives a rotation of the respective shaft 58a or 58d around its axis.

Figure 9:
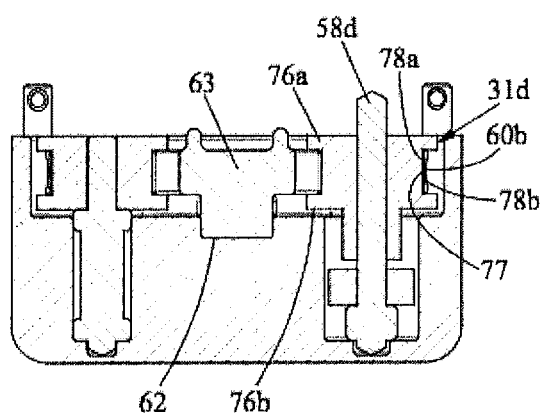
FIG. 9 is a cross-sectional view along the line IX-IX from FIG. 5.

Each of the shafts 58a-58d also supports a respective pulley 31a-31d. As can be seen in FIG. 9, the pulley 31d comprises two superimposed discs 76a, 76b, along the shaft, between which extends a drive surface 77 for the belt 60b. The discs serve as upper and lower stops for the belt. The same description applies to all the pulleys. The belt 60b comprises a toothed inner face 78, cooperating with the drive surface 77, and an opposite outer face 78b. The outer face 78b is intended to cooperate with the catheter. It is composed of a suitable material, able to withstand the deformations the belt undergoes from the applied movement, and remaining integral with the catheter, even when wet. A suitable elastomer, rubber, or silicone, for example, is used. Returning to FIG. 5, a channel 59 is defined between these four pulleys, and can receive a catheter. The two pulleys 31a and 31b are associated with each other by a belt 60a stretched between these two pulleys. Likewise, a belt 60b is stretched between the two pulleys 31c and 31d.

In a given position of the drive module, each belt comprises a strip portion 61a and 61b extending in the channel and engaged with the catheter passing through the channel. The strip parts are elongated in the longitudinal direction and run in that direction when the translation motor is actuated.

An adjustment mechanism 34 makes it possible to adjust the module to the elongated flexible device to be driven. Thus, the adjustment mechanism 34 may be used to fine tune the drive system for different identical catheters, or to greatly modify the channel width when the module must be adapted to drive a catheter or a guide with a much smaller diameter. In the example presented, the adjustment mechanism 34 comprises a longitudinal slide 62 formed in the bottom part 54 of the shell 21, extending transversely to the longitudinal direction X, and a plunger 63 suitable for sliding in said slide 62 toward or away from the channel. The plunger 63 is arranged inside the periphery of the respective belt 60a or 60b, and has a tensioning surface 81 that cooperates with the inner face 78a of the belt so as to move the strip part 61a or 61b of the belt transversely to the direction X. The plunger 63 may be fastened in the adjusted position by any appropriate means, such as by a screw 64 screwed into a bore 65 in the bottom part 54. The plunger has a length (along the axis of the slide) greater than the diameter of the pulleys. Thus, whatever the position of the plunger relative to the belt within the adjustment range, the belt tension remains substantially the same.

The belts have an inner surface 78a suitable for being driven by the drive pulley, and for sliding along the surfaces of the plunger 63, cooperating with it. Such an inner surface is, for example, toothed. The outer surface 78b of the belt is made of a material suitable for cooperating with the soft and moist elongated medical device, and may, for example, comprise a suitable elastomeric material.

When in use, a cover 66 is assembled to the bottom part 54 of the shell 21, to keep the various parts that have just been described in the shell. In the present embodiment, the shafts 58a and 58d are drive shafts and are driven, during rotation of the shaft 28, such that the strip parts 61a and 61b travel in the channel in the same direction, for a given rotation of the translation drive motor. Thus, these strip parts directly apply movement to the elongated flexible device. The shafts 58b, 58c are driven, not directly by the translation motors, but by the belts.

As shown in FIG. 2, the exit 18 from the second system comprises a mounting device 35 allowing free rotation of the catheter 6 around its elongation axis relative to the second system, and the driving of the second container 17 during translation of the catheter 6 in its direction of elongation. According to a purely illustrative example of the mounting device 35, the distal end of the catheter 6 is fastened to a grooved ring that is inserted into a complementary orifice formed in the second container. The ring is thus free to turn relative to the second container around an axis of elongation of the guide 37. The ring may have a shape that flares toward the catheter 6, to facilitate manual gripping by a user.

According to a variant, the flap could be replaced by an open ring sunk into the second container.

Note that the embodiment presented in FIG. 2 may for example be modular, namely, the first system 12 and the second system 13 may be sold separately and assembled for patient examination purposes.

There may further be a third system insertable into the second system and concentric with it around the Z-axis, for insertion of an interventional catheter into the patient, in addition to the guide and catheter. Similarly, the third system comprises a container able to contain a fluid, a drive mechanism, and an exit opening into the second system. The systems are arranged such that the element to be inserted that has the largest diameter (usually the catheter) is placed in the outer system, and the element to be inserted that has the smallest diameter (usually the guide) is placed in the inner system, the interventional catheter therefore being placed in the intermediate system.

Furthermore, each system can itself be made modular, that is, the electric motors can be provided permanently mounted on the robot, and the rest of the system can be disassembled from it and replaced by a disposable part with no electric motor. In this way, the costs associated with reusing the system are greatly reduced, because the most expensive elements can be kept from one use to the next (they may possibly be sterilized or decontaminated before subsequent use).

The above description has been given with reference to the first drive system 12. A similar description is possible for the second drive mechanism 19. Similarly to the first sterile barrier 44, a second sterile barrier 144, independent of the first, can be slid between the plate 42 and the corresponding module. The second sterile barrier 144 will cover the motors 24 and 26 of the second system and the plate 39. However, the tube 14 and the container 17 will be placed on top.

In one particular embodiment, as shown in FIG. 6 in particular, the system allows simple and inexpensive repeated use. In particular, a major part of the system is sheltered by a sterile barrier, as explained above, and thus does not require complex and expensive repeated sterilization operations. With respect to the smaller part of the system intended to come in contact with the patient via a tubular elongated flexible medical device, this is composed exclusively of disposable parts, sterilizable parts, and quick connecting parts, themselves sterilizable. In particular, in the presented example of a drive module, only the belts are made as disposable parts. For the assembly parts, there may for example be elastically deformable parts that hold the sterilizable parts together, if applicable with the possibility of movement relative to each other. One example might be the removable device formed of pins 48, already described above in relation to FIG. 3, whose first arm slides into an appropriate opening in an arm 46a, 46b of the base and forms a part of the rotary bearing for the movable assembly, and whose second arm is elastically deformed for retention. As another example, the U-shaped pins 67 have their two parallel arms inserted into the corresponding openings 68 in the retaining cylinders 69 of the rotational or translational shafts 51, 52. These shafts each comprise a groove 70 that cooperates with each of the arms of the corresponding pin 67 to prevent travel of the shaft relative to the cylinder in its extension direction, while allowing its rotation.

There is similar pin 71 to cooperate with a groove 72 in the shaft 28 to prevent the shaft 28 from coming out of its receiving cylinder.

There may be similar systems to hold the cover 66 on the bottom part 54 of the movable assembly. Thus the bottom portion 54 may comprise four dowels 73 on the upper surface. The cover 66 is inserted onto said dowels through the corresponding openings 74 arranged in each corner. The dowels 73 are themselves provided with through-openings 75 aligned in pairs, able to receive one arm of a pin (not shown) similar to the pins 48 described above.

The base 43 may be fastened to its support in a similar manner, by retaining support studs passing through the bores 41 of the base 43 with elastically deformable retaining means.

Thus, the assembly parts and assembled parts are "sterilizable" parts in that they are easily cleanable in their entirety, with no areas inaccessible to cleaning.

An example of a use of the device depicted in the figures is described below. It should be noted that, in FIG. 2, practically the entire catheter has been inserted inside the patient. A surgeon punctures an artery, for example the femoral artery at the inguinal fold, and places a short hose with a valve constituting an access port between the exterior and the artery, commonly called a Desilet catheter. The winder/unwinder from FIG. 2 is placed in proximity to the patient and is connected to the computer 4. The winder/unwinder 5 already contains a preservative fluid in which a catheter is immersed in the first system, and in which a guide that is insertable into the catheter is immersed in the second system. By opening the adjustment mechanism 34 of the first system to the maximum, the catheter can be moved until the surgeon can insert it manually through the Desilet catheter into the artery. Then, from the computer 4, the surgeon controls the translational electric motor of the second system to guide the guide 37 through the outlet 18, into the catheter 6, until the first end of the guide arrives, inside the patient, at the first end of the catheter. During this operation, the X-ray source 8 can emit radiation that has no effect on the surgeon 2, and the image from the detector 10 can be displayed on the computer screen 11.

So that the end of the catheter reaches the location of interest inside the body of the patient 1, the surgeon 2 controls the following functions from the computer 4:

translational movement of the guide: by activating the translational electric motor 26 of the second system, which rotationally drives a set of drive parts, in particular the translation gear ring 22, the intermediate gear 30, the shaft 28, the sprockets 32a and 32b, and thus the drive pulleys 31a to 31d and therefore the belts 60a and 60b, which generate translational movement of the guide in its elongation direction inside the catheter 6, the rotation of the guide around the longitudinal axis of the guide, by controlling the actuation of the rotational electric motor 24 of the second system, and thereby a set of drive parts, particularly the rotational gear 25 and the rotational gear ring 23 that rotates the movable assembly and guide relative to the bearings 20a and 20b of the second system, and thereby rotates the guide held on the assembly by the belts 60a and 60b, the translational movement of the catheter in its direction of elongation, controlled similarly to the guide translational control described above (because of the connection of the second end of the catheter to the mounting device 35, said translation drives the free rotation of the second system around the Z-axis relative to the first container), and the rotation of the catheter, controlled as previously described for the guide, the mounting device 35 allowing the catheter 6 to turn about its elongation axis without affecting the guide 37 or the second container.

In practice, due to the use of gears, the translation and rotation controls are partially connected. FIG. 11a depicts a starting position within the frame of reference of the part. If only the rotation motor is made to operate, the movable assembly 40 will turn about the axis X as shown. Due to the engagement between the sprockets 30 and 28, if the sprocket 30 is held stationary (i.e., the translation motor is not made to operate), the sprocket 28 will also turn about its axis. This is illustrated in FIG. 11b by an arrow indicating a reference tooth of the gear 28.

Thus, the rotation control generates rotation of the shaft 28 within the frame of reference of the movable assembly, and thus rotation of the belts (translation of the catheter).

To generate a pure rotational movement of the catheter simultaneously with the rotation control, a translation control suitable for counterbalancing that travel is applied. The two controls are applied in a predetermined ratio (characterized by the gears coming into play). A pure rotational movement is generated when the reference tooth of the sprocket 28 remains pointed in a constant direction within the frame of reference of the movable assembly, as shown in FIG. 11c.

If applicable, gear movement detection is used to adapt that ratio.

However, in the case of a translation motor control being applied, no rotation is generated in the module and a pure translational movement of the catheter is generated.

Thus in some embodiments, it is possible to jointly control the translation of the guide and the catheter by simultaneously controlling the two corresponding motors.

Commands for both translation and rotation can of course be carried out in one direction or the other, to move the guide and the catheter to or from the site.

The second container can be rotated relative to the first container by rotating the tray 39 with a specially dedicated electric motor 75 connected below the tray. This dedicated motor can particularly be used to guide the tray after use.

Furthermore, in one embodiment also comprising the insertion of an interventional catheter intended to provide a certain function at the site, the operations and variants described above can also be implemented for the third system.

Figure 7A:
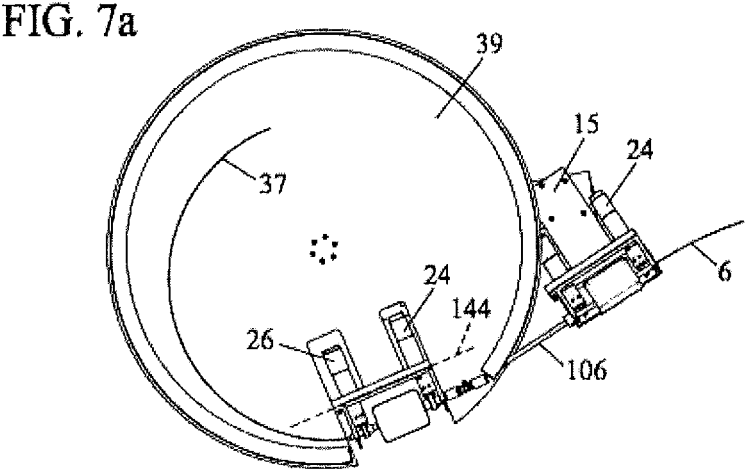

Thus, FIG. 7a is a top view of the system in a position where the catheter has almost completely entered the body of the patient.

Figure 7B:
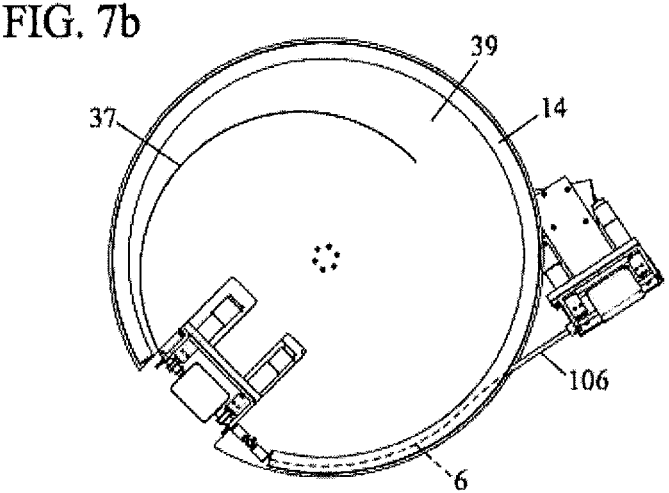
Figure 8:
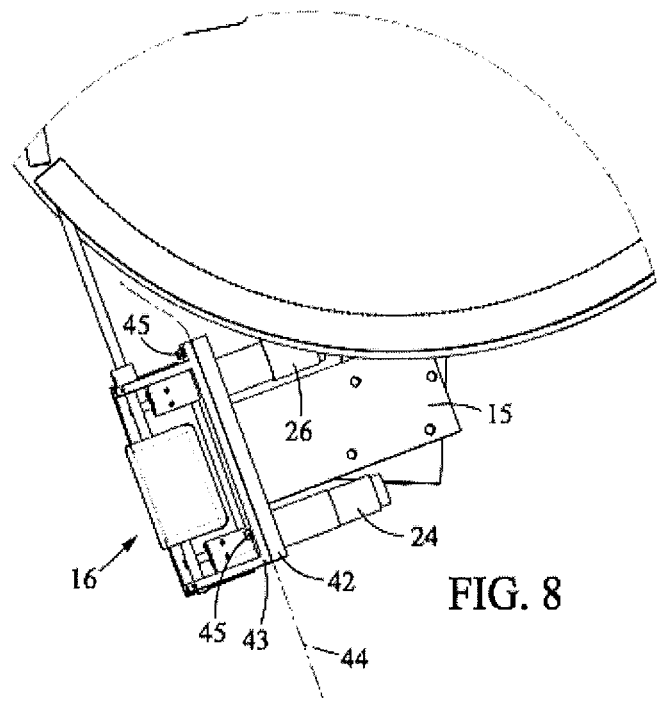
FIG. 8 presents an enlargement of FIG. 2 showing the placement of a sterile barrier.

As shown in FIG. 7b, when one wants a portion of the catheter to exit the body of the patient, in addition to applying translational movement in the direction opposite direction X using the drive system, rotation is applied using the motor 75 of the tray 39, so that the catheter 6 returns into the container 14. To translationally drive the catheter, a command to the catheter translation motor and a command to the tray motor 75 are thus simultaneously applied in a predetermined ratio, so that the length of travel of the catheter corresponds exactly to the length of entry/exit of the catheter in the tube 14.

Furthermore, if translational movement of the catheter relative to the patient is generated, as explained above, by controlling the catheter translation motor and the motor 75 of the tray 39, the rotation of the tray 39 drives the translation of the guide relative to the patient, if the second drive system is inactive during this step. If, on the contrary, it is desired that the guide remain motionless in the patient during this step, the translation motor of the guide is controlled in order to move it relative to the second system, according to a predetermined ratio with the translation control of the catheter.

The various motorizations to be applied to the different motors in order to obtain the various unit movements are summarized in the table below:

|  | Guide | | Catheter | | |
| --- | --- | --- | --- | --- | --- |
|  | Translation | Rotation | Translation | Rotation | Tray Rotation |
| Translation, guide only | X | | | | |
| Rotation, guide only | X | X | | | |
| Translation, catheter only | X | | X | | X |
| Rotation, catheter only | | | X | X | |
| Translation, catheter and guide | | | X | | X |
| Rotation, catheter and guide | X | X | X | X | |

The gear motors are equipped with pulse encoders giving the movements. Such movements are measured by any appropriate means.

In the case of the implementation of a third system, the above teachings will be adapted.

Thus, in general, the robotic catheter system comprises:
a central processing unit,
at least a first, second, and third control line respectively suitable for sending a command to a first, second, and third drive motor of the same catheter (the translation and rotation motors and the tray motor),
wherein the first and second control lines (translational and tray) are controlled according to a first predetermined ratio for controlling a pure translational movement of the catheter along its axis, and wherein the first and third control lines (translational and rotational) are controlled according to a second predetermined ratio for controlling a pure rotational movement of the catheter along its axis.

To generate a pure rotational movement of a device, the translation motor of the drive system associated with that device is also controlled according to a predetermined ratio.

To generate a differential translational movement on the two devices, the translation motors of the two drive systems and the tray motor are controlled according to predetermined ratios.

After use, the system can be disassembled as follows:
the base 43 is disassembled from its support by removing the quick connect systems serving for that assembly,
the pins 48 are removed, so as to disassemble the base 43 from the movable assembly 40 by removing the movable assembly out of the slots 47,
the quick fastening devices 67 are removed so as to disassemble the rotational and translational shafts 51, 52 from the base 43,
the sleeve 154 is removed by sliding it along the downstream shaft 149,
the cover 66 is removed from the bottom part 54, by removing the pins passing through the openings 75 in the bottom part,
the plungers 63 are removed from the bottom part 54,
the shafts 58a-58d respectively supporting the pulleys 31a-31d and the belts are removed from the bottom part 54, and the belts are removed from said pulleys,
the shaft 28 is removed from the bottom part 54 by removing the pin 74 and sliding through the opening 29,
the adjustment screws 75 are unscrewed.

The disposable elements may be discarded, and the various non-disposable elements are small parts with simple shapes that can be sterilized.

The disposable elements of the robot, such as the tube 14 containing the catheter removed from the body of the patient, or the connecting device 35, may also be disassembled and discarded or sterilized as appropriate, and the sterile barriers are discarded.

For a subsequent operation, the system can be assembled by a sterile operator, through a sequence that is the reverse of the sequence of operations described above for disassembly.

The adjustment system 34 may be implemented in any appropriate manner, such as a mechanical system using screws 64 or, alternatively, a piezoelectric or other system.

Figure 10:
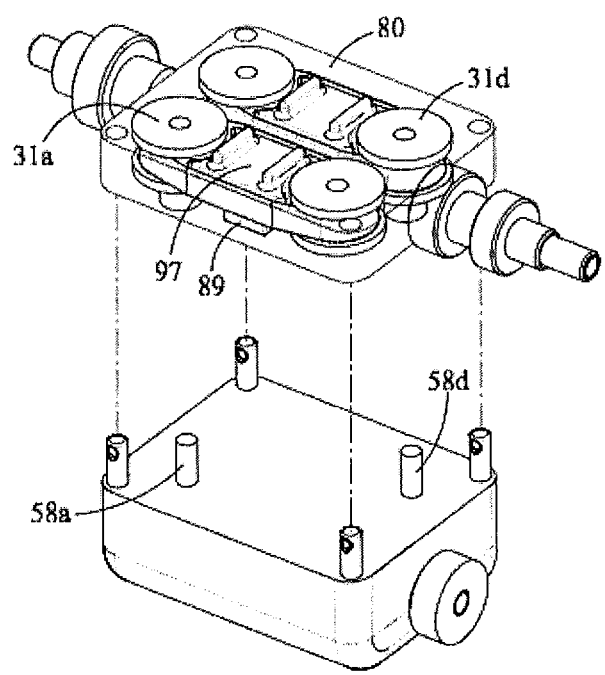
FIG. 10 is an exploded schematic perspective view of a second embodiment of a shell.

Although in the embodiment shown above, some elements are presented as independent, in a variant some of these elements may be assembled or pre-assembled to each other, if appropriate. For example, as shown in FIG. 10, the pulleys 31a-31d may be (movably) pre-assembled together on a common base 80 for assembly on drive shafts 58a-58d (if applicable, removably) ready to assemble on the bottom part 54. This part 80 comprising the pulleys and, if applicable, the belts, may be disposable.

Figure 10A:
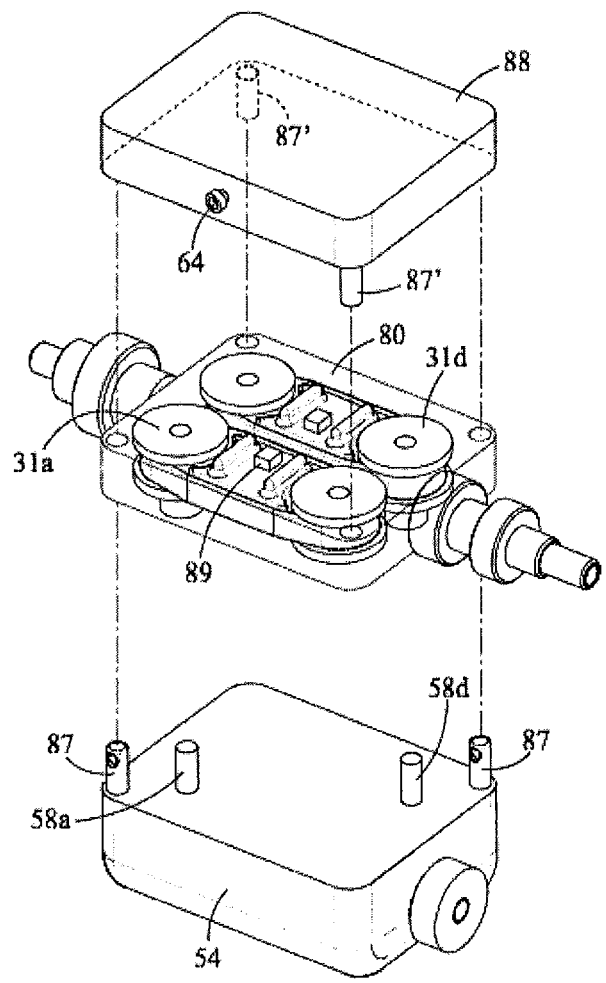
FIG. 10a is a view similar to FIG. 10 for a variant embodiment.

Another variant embodiment is depicted in FIG. 10a. Two end pins 87 are used to assemble the bottom part 54 to the disposable part 80, and a lid part 88 is similarly assembled to the disposable part 80 using two end pins 87', for example supplied at an angle opposite that of the pins 87. The part 80 is thus maintained between the bottom portion 54 and the lid part 88. The lid part 88 may also comprise the plunger adjustment system 34. Thus, unlike the embodiment from FIG. 10 where the area 89 where the plungers are driven by the screw 64 (not shown) is located below the body 97 of the plunger, in FIG. 10a that area 89 is above the body of the plunger, so as to interact with the screw 64 mounted in the lid 88.

Thus, according to one aspect, the movable assembly 40 comprises:
a bottom part 54 comprising at least one drive shaft, and
a part 80 comprising at least said pulleys. The part 80 is assemblable by quick fastening to the bottom part, with the motorized pulley cooperating with the drive shaft during this assembly.

Thus, in the two above embodiments, the axis around which the movable assembly rotates relative to the base, and the median axis of the catheter at the place where it is driven by the belts, are equal and parallel to the longitudinal direction X.

Figure 12:
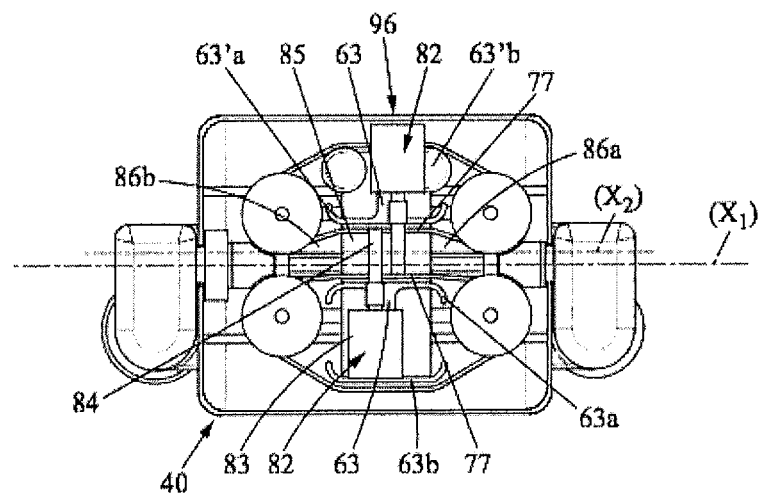
FIG. 12 illustrates a third embodiment.

According to another embodiment, shown in FIG. 12, the rotational axis X1 and the translational drive axis X2 are offset with respect to each another in a direction transverse to the longitudinal direction. The translational drive axis X2 is defined as the median axis between the two drive surfaces 77 in use, which are themselves defined by the surfaces of the belts. The position of the axis 52 in use is thus defined by the position of the plungers 63. In other words, the channel comprises a central portion 85 extending along the axis X2, and entry 86a and exit 86b portions forming a non-zero angle with the longitudinal direction. Thus, there is a lateral adjustment system 96 that defines the position of the axis X2 with respect to the rotational axis X1. The offset value between the two axis can thus be adjustable. The plungers 63 serve not only to define the width of the channel, the clamping force applied to the catheter, or the tension of the belts, but also the offset of the axis X1 and X2.

In the embodiment presented, the lower plunger 63 comprises an inner portion 63a and an outer portion 63b that can be fixed in a plurality of different positions along the transverse axis relative to the inner portion 63a. This adjustment makes it possible to adjust the tension of the lower belt. The upper plunger 63 comprises an inner portion 63'a, similar to the inner portion 63a, and an outer portion 63'b. The outer portion 63'b here is independent from the inner portion 63'a, and implemented for example as two tensioner rollers. If necessary, they may be movable so that their displacement along the transverse axis allows adjusting the belt tension. Displacement of the two inner portions in opposite directions allows adapting the system to the width of the device to be driven, and also adjusting the clamping force applied to said device. Displacement of the two inner portions in the same direction allows adjusting the axis offset.

On rotation of the movable assembly 40 on the base 43, said axis offset makes it possible to obtain the desired rotational travel of the end of the catheter inside the patient.

If applicable, the axis offset may be varied during the use of the robot. Thus, remote controlled motorization devices 82 may be used by the user to move each plunger to the desired position. One exemplary embodiment comprises a gear motor 83 driving a worm gear 84 turning in a nut attached to each plunger. Variants other than the ones described are possible, such as having the two gear motors located on the same side of the channel, and/or using a cylinder or a micropositioner. According to another variant, rather than independently adjusting the position of each plunger, the two mechanisms can be connected so as to have one control for the position of the axis X2 and another control for the distance of the plungers relative to said axis (width of the catheter and its clamping). Finally, note that, as a variant, the axis offset could be used for other types of translational drive systems integrated on a rotary shell, such as a system with one or more drive roller(s) having a non-extended drive surface.

Figure 13:
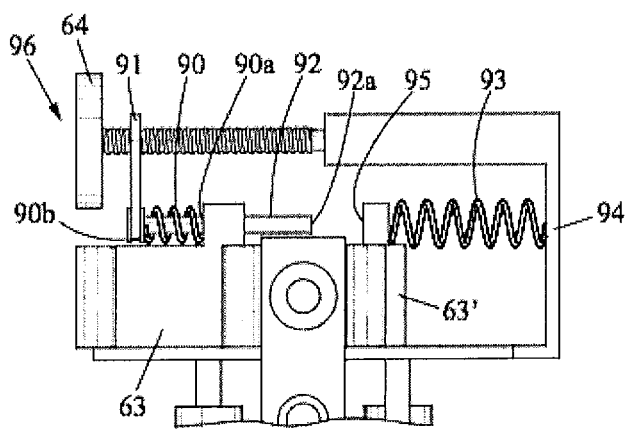
FIG. 13 is a partial front schematic view illustrating a fourth embodiment.

According to the embodiment from FIG. 13, a single lateral adjustment system 96 is used, firstly for clamping the catheter with a predetermined force (for example 6 Newtons), and then, continuing the actuation from the system control, offsetting the drive axis X2 relative to the rotational axis X1. As an example, there is a first spring 90 (or any other suitable elastic element) extending between a first end 90a applying force against a first plunger 63, and a second end 90b applying force against a slider 91. The slider itself is mounted to move along the transverse travel axis of the plunger, for example by means of the screw 64. The spring 90 is also supported by a rod 92 having a stop end 92a. There is a second spring 93 (or any other suitable elastic element) between the frame 94 and the second plunger 63'. The second plunger 63' is equipped with a stop surface 95 facing the stop surface 92a of the rod.

The actuation of the screw 64 generates the translation of the slider 91 and thus the travel of the first plunger 63 until the stop end 92a of the rod abuts the stop 95. In this position, the catheter is subject to the predetermined clamping force according to the compression of the spring 90. Continued actuation of the screw 64 will cause compression of the spring 93, and consequently the travel of the first and second plungers in the direction of the frame. Thus, the continued actuation of the screw 64 will cause the offset of axis X2.

Note that the screw 64 can be driven manually, or in a motorized manner such as by a battery-powered motor, for example, or mechanically by a remote actuator, in a predetermined position of the module (called the adjustment position), where the actuator is in a position able to carry out such driving.

In a variant of the screw 64, other systems can be used, such as rack systems for example.

Thus a module is provided for driving an elongated flexible medical device in a first direction, comprising a base and a movable assembly mounted to rotate on said base around a first axis extending in the first direction, the movable assembly comprising a support,
  wherein the module comprises:
  a channel formed in the support, extending in the first direction,
  on each side of the channel:
    at least a first and a second drive device borne by the support, each having a face suitable for cooperating with the flexible medical device,
  wherein said channel comprises a portion along a second axis, parallel to the first axis and offset relative to it.

To the extent possible, a system is preferred that is compatible with the principles of simple assembly/disassembly and sterilization (or implemented as disposables) stated above for the first two embodiments.

The invention claimed is:

1. Drive module for driving along a first direction an elongated flexible medical device, wherein the elongated flexible medical device is elongated in a first direction, wherein the driving module comprises a base and a movable assembly mounted to rotate on said base about the first direction, wherein the movable assembly comprises a support, wherein the driving module comprises:
  a channel formed in the support, said channel extending in the first direction, said channel designed to receive the elongated flexible medical device,
  on a first side of the channel:
  at least a first and a second pulleys, each of said at least a first and a second pulleys on the first side of the channel having a drive surface and each of said at least a first and a second pulleys on the first side of the channel being borne by the support,
  an elongated strip comprising a first face and an opposite second face, the first face of the elongated strip on the first side of the channel cooperating with the drive surface of the said at least a first and a second pulleys on the first side of the channel, the elongated strip on the first side of the channel being stretched by the said at least a first and a second pulleys on the first side of the channel with an elongated portion extending into the channel in the first direction,
  on a second side of the channel: 2
  at least a first and a second pulleys, each of the said at least a first and a second pulleys on the second side of the channel having a drive surface and each of the said at least a first and a second pulleys on the second side of the channel being borne by the support,
  an elongated strip comprising a first face and an opposite second face, the first face of the elongated strip on the second side of the channel cooperating with the drive surface of the said at least a first and a second pulleys on the second side of the channel, the elongated strip on the second side of the channel being stretched by the said at least a first and a second pulleys on the second side of the channel with an elongated portion extending into the channel in the first direction,
  wherein the second face of the elongated strip on the first side of the channel and the second face of the elongated strip on the second side of the channel are each adapted to engage the elongated flexible medical device to drive the flexible medical device along the first direction, at least one of the said at least a first and a second pulleys on either side of the channel being a motorized pulley.

2. Drive module according to claim 1, further comprising an adjustment device placed between the first and the second pulleys on one side of the channel, comprising a tensioning surface cooperating with the first face of the elongated strip on said side of the channel and movable relative to the channel along an adjustment direction transverse to the first direction.

3. Drive module according to claim 1, wherein the first face of the elongated strip on one side of the channel has sprockets and wherein the drive surface of the motorized pulley has teeth that mate with said sprockets.

4. Drive module according to claim 1, wherein the movable assembly comprises:
  a bottom part comprising at least one drive shaft, and
  a disposable part in which said channel is formed, the disposable part comprising at least said at least a first and a second pulleys on the first side of the channel and on the second side of the channel, the disposable part being assemblable on the bottom part, the motorized pulley cooperating with said drive shaft.

5. Drive module according to claim 1, wherein the movable assembly is mounted to rotate on the base about a first axis, and wherein the channel comprises a portion formed in the support along a second axis, parallel to the first axis and offset relative to it.

6. Drive module according to claim 5, comprising a lateral adjustment device adapted to adjust an offset between the first axis and the second axis.

7. Drive module according to claim 6, wherein the lateral adjustment device comprises a control adapted to cause clamping of the elongated flexible medical device during a first part of the drive stroke, and to adjust said offset between the first axis and the second axis during a second part of the drive stroke after the first part.

8. Drive module according to claim 1, comprising a set of driving parts cooperating with each other to transmit a movement from a motor to the motorized pulley.

9. Drive module according to claim 1, composed of said elongated strips on the first side of the channel, said elongated strip on the second side of the channel, of sterilizable parts, and of elastically deformable removable assembly parts suitable to hold the sterilizable parts together with freedom of movement relative to each other.

10. Robotic system comprising:
   a drive module according to claim 1,
   a container suitable to contain an elongated flexible medical device in a sterile aqueous condition, and in communication with said channel,
   a motor cooperating with the motorized pulley.

11. Robotic system according to claim 10, further comprising a sterile barrier, the motor cooperating with the motorized pulley through the sterile barrier.

12. Robotic system according to claim 10, comprising at least three motors suitable for generating different movements to at least one elongated flexible medical device, and comprising a central processing unit suitable for simultaneously controlling at least two motors according to predetermined ratios.

13. Drive module for
   driving along a first direction an elongated flexible medical device, wherein the elongated flexible medical device is elongated in a first direction, wherein said drive module comprises a base and a movable assembly mounted to rotate on said base about the first direction, wherein the movable assembly comprises:
   a bottom part comprising at least one drive shaft, and
   a disposable part comprising a support in which said a channel is formed, said channel extending in the first direction, said channel being designed to receive the elongated flexible medical device, the disposable part comprising at least said pulleys a drive device on both sides of the channel,
   said drive devices being borne by the support, said drive devices having a face engaging the elongated flexible medical device, one of said drive device being a motorized drive device, the disposable part being assemblable on the bottom part, the motorized drive device cooperating with said drive shaft to drive the elongated flexible medical device along the first direction.

14. Drive module for
   driving along a first direction an elongated flexible medical device, wherein the elongated flexible medical device is elongated in a first direction, wherein the drive module comprises a base and a movable assembly mounted to rotate on said base about a first axis extending in the first direction, the movable assembly comprising a support, wherein the drive module comprises:
   a channel formed in the support, said channel extending in the first direction, said channel being designed to receive the elongated flexible medical device
   on a first side of the channel:
   at least a first and a second drive devices borne by the support, each of said at least a first and a second drive devices on said first side of the channel having a face suitable for engaging the elongated flexible medical device,
   on a second side of the channel:
   at least a first and a second drive devices borne by the support, each of said at least a first and a second drive devices on said second side of the channel having a face suitable for engaging the elongated flexible medical device wherein said channel comprises a portion along a second axis, parallel to the first axis and offset relative to the first axis.

15. Drive module according to claim 14, wherein said portion is offset relative to the first axis by an offset, and the drive module further comprising a lateral adjustment system suitable for varying an amplitude of said offset.

* * * * *